United States Patent
Davey et al.

(10) Patent No.: US 6,500,989 B1
(45) Date of Patent: Dec. 31, 2002

(54) PREPARATION OF CARVONE

(75) Inventors: Paul Nicholas Davey, Kent (GB); Christopher Paul Newman, Kent (GB); William Alexander Thiam, Kent (GB); Chi-Lam Tse, Kent (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/913,877

(22) PCT Filed: Mar. 27, 2000

(86) PCT No.: PCT/GB00/01173

§ 371 (c)(1),
(2), (4) Date: Dec. 4, 2001

(87) PCT Pub. No.: WO00/58253

PCT Pub. Date: Oct. 5, 2000

(30) Foreign Application Priority Data

Mar. 30, 1999 (GB) ............................................... 9907194

(51) Int. Cl.⁷ ............................................... C07C 45/00
(52) U.S. Cl. ....................... 568/338; 568/361; 568/366
(58) Field of Search ................................ 568/338, 361, 568/366

(56) References Cited

U.S. PATENT DOCUMENTS 2,837,570 A * 6/1958 Linder et al.
3,293,301 A * 12/1966 Derfer et al.

FOREIGN PATENT DOCUMENTS

EP 0 555 561 8/1993

OTHER PUBLICATIONS

Database WPI, Section Ch, Week 197542 Derwent Publications Ltd., London, GB; AN 1975–69758W, XP002140907 & JP 50 071648 A (Hasegawa Co Ltd. T), Jun. 13, 1975 abstract.

Database WPI, Section Ch, Week 199103, Derwent Publications Ltd., London, GB; AN 1991–017088, XP002140908 & IL 77 359 A ( YEDA Res 7 Dev Co Ltd.), Nov. 5, 1990, abstract.

* cited by examiner

*Primary Examiner*—Sreeni Padmanabhan
*Assistant Examiner*—Sikarl A. Witherspoon
(74) *Attorney, Agent, or Firm*—Morgan, Lewis & Bockius LLP

(57) ABSTRACT

A process for the preparation of carvone comprises hydrogenating carvoxime in the presence of a selecively poisoned catalyst. Preferred catalysts include noble metals supported on inorganic materials poisoned with a catalyst modifier. In a preferred embodiment of the process defined herein, the crude carvone reaction product produced in accordance with the process of the invention, is purified by treating the crude carvone product with an organometallic compound $M(X)_n$ wherein M is a polyvalent metal, n is the valence of M and X denotes an inorganic or organic atom or group.

22 Claims, No Drawings

PREPARATION OF CARVONE

This application is the National Phase of International Application PCT/GB00/01173 filed Mar. 27, 2000 which designated the U.S. and that International Application was published under PCT Article 21(2) in English.

FIELD OF INVENTION

This invention relates to the preparation of carvone (5-isopropenyl-2-methyl-2-cyclohexen-1-one) and in particular to the conversion of carvoxime (5-isopropenyl-2-methyl-2-cyclohexen-l-one oxime) to carvone.

BACKGROUND OF INVENTION

L-Carvone (5(R)-isopropenyl-2-methyl-2-cyclohexen-1-one) is widely used as an odorant or flavouring component for tooth paste or powder, chewing gum, mouthwashes etc. In these dental applications, it is important the carvone has a high purity and, in particular, it is important that hydroxy compounds, such as α-terpineol, a common by-product of carvone synthesis, are present at a low level. These materials often cannot be separated from carvone by distillation and a laborious, costly and effluent-intensive bisulphite extraction and wash is generally needed to remove the contaminants. An alternative method which is suitable for separating by-products such as α-terpineol is disclosed in U.S. Pat. No. 5,302,759. The process described in this patent utilises the reaction between an organometallic compound and an alcohol to bring about a separation of an alcohol from a ketone. Unfortunately, this purification process is not economical when the amount of hydroxy compounds present in the carvone is relatively high.

In one process for preparing carvone, carvoxime is hydrolysed by transoximation under acidic conditions with sulphuric acid and acetone. While the hydrolysis affords reasonable yields of carvone, substantial amounts of α-terpineol, formed from limonene, and hydroxycarvone are formed. Moreover, stoichiometric amounts of acetoxime, a suspected carcinogen, are formed as side products and a large amount of sulphate effluent is produced. Hence, the process, although practical, carries a substantial environmental burden. Furthermore, the amount of α-terpineol and hydroxycarvone generated from the process means that the purification method disclosed in U.S. Pat. No. 5,302,759 cannot be applied economically and hence a bisulphite treatment is needed to purify the resulting carvone in order to produce dental quality product. This results in a further environmental burden.

In the search for an environmentally friendly carvone production process, one of the important objectives is elimination of the formation of the toxic acetoxime which is produced in the above-mentioned process, as shown in the following scheme:

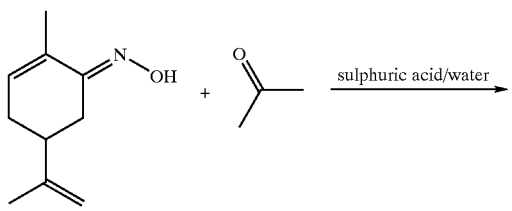

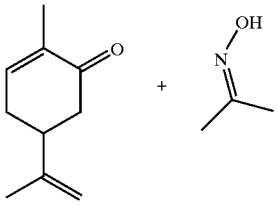

One solution is a reductive deoximation of carvoxime which is described in Japanese Patent Application JP 50 071 648 in which metallic iron in aqueous carboxylic acid is used for the reduction. An ammonium salt is the side product of this process, and the production of acetoxirne is therefore eliminated. However, a stoichiometric amount of iron is used and stoichiometric amount of iron salt/iron oxide is formed as a side product.

Catalytic hydrogenation is a well-known and useful industrial technique that can be applied on a manufacturing scale and which uses a cheap reducing agent, namely hydrogen. The problem with using hydrogenation in the reductive deoximation of carvoxime is that the reagent may not be selective. Thus, the two olefin functional groups can be saturated readily to produce dihydrocarvones and/or tetrahydrocarvones.

Hydrogenation has been used to synthesise olefins from alkynes, the hydrogenation being better known as Lindlar's hydrogenation (Lindlar, H.; Dubuis, R. Organic Synthesis Coll. Vol. V, 1973, p.880). Lindlar's hydrogenation normally uses a palladium on calcium carbonate or palladium on barium sulphate catalyst that is selectively poisoned by, for example, a lead salt or quinoline.

It has now been found that the formation of hydroxy compounds such as a-terpineol during the synthesis of carvone can be minimised by using a hydrogenation process to convert carvoxime to carvone. Surprisingly, hydrogenation catalysts, such as Lindlar's catalyst, have been found to efficiently convert carvoxime to carvone.

SUMMARY OF INVENTION

According to the invention, there is provided a process for the preparation of carvone comprising hydrogenating carvoxime in the presence of a selectively poisoned catalyst.

The process is illustrates by the following reaction scheme.

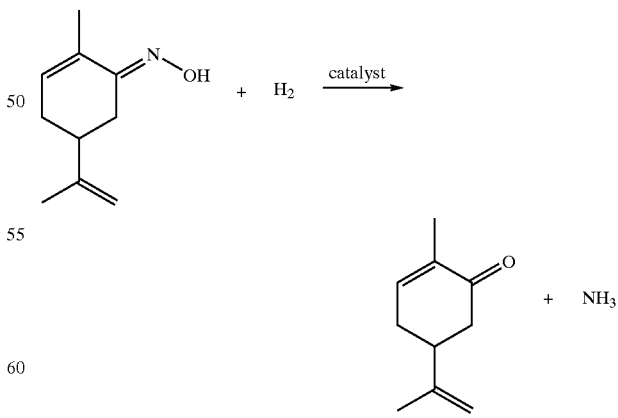

The reaction product, carvone, can exist as optical isomers. The more useful and preferred, isomer is L-carvone although the process is equally suitable for producing D-carvone.

The carvone produced using this process contains a relatively small amount of hydroxy compounds, particularly a-terpineol, and therefore the process of U.S. Pat. No. 5,302,759 can be economically employed to purify the product. Therefore, in a preferred embodiment, the process of the invention further comprises a purification of the reaction product carvone by treating the crude carvone product with an organometallic compound $M(X)_n$ wherein M is a polyvalent metal, n is the valence of M and X denotes an inorganic or organic atom or group.

The starting material, carvoxime, in the process of the invention, can be prepared by any suitable method. Typically, limonene (d-) is reacted with nitrosyl chloride to give a chloronitrosylated product which, on dehydrochlorination and tautomerisation, yields carvoxime.

This crude carvoxime product is then converted to carvone using the process of the invention. Alternatively, the crude carvoxime may be purified before use. Carvoxirne is hydrogenated by heating the carvoxime in the presence of a hydrogen source and a selectively poisoned catalyst.

The preferred reaction temperature is in the range 80° C. to 180° C. and, more preferably in the range 120° C. to 155° C.

A suitable, and preferred, hydrogen source for use herein is hydrogen gas. In this case, the reaction is preferably carried out at a pressure above atmospheric pressure, typically at a pressure in the range 1.0 to 10.0 MPa, and, more preferably, in the range 4.0 to 6.0 MPa.

Alternatively, the hydrogen source can be any compound which is a hydrogen donor. Suitable examples include formic acid; formate salts such as sodium formate; secondary alcohols such as isopropanol; cyclohexene; cyclohexadienes; tetralin; teipinolenes; limonene; or other unsaturated cycloalkanes. Preferably, the hydrogen donor is formic acid which is buffered by a salt. Suitable salts for use herein include, but are not limited to sodium acetate, bicarbonates, carboxylates, hydrogen phosphate, dihydrogen phosphate or ammonium salts. Preferably, the salt is sodium acetate.

When the hydrogen source is a hydrogen donor, the reaction can be carried out at atmospheric pressure, and so may be performed using ordinary apparatus.

In accordance with the invention, the reaction is carried out in the presence of a poisoned catalyst. By "poisoned catalyst" is meant a catalyst which is active in promoting conversion of the oxime group to a ketone group but does not hydrogenate the carbon-carbon double bonds in the carvoxirne molecule significantly. Typically the catalyst is a supported metal catalyst, especially a noble metal catalyst and effective catalysts include, but are not limited to, metals, such as palladium, supported on a material, such as barium sulphate or alumina, which have been poisoned by mixing with a catalyst modifier such as a lead compound or quinoline. A particularly preferred catalyst is palladium on barium sulphate poisoned by red lead oxide ($Pb_3O_4$).

Generally, the catalyst will be present in an amount in the range 0.1% to 10.0% by weight of carvoxime and preferably in an amount in the range 3.0% to 6.0% by weight of carvoxime.

The hydrogenation of carvoxirne produces ammonia as a by product and it is preferable to add an acid to the reaction mixture to neutralise the ammonia produced. Many acids can be used, including organic and inorganic acids but preferred acids include carboxylic acids such as acetic acid or formic acid.

The hydrogenation of carvoxime using the process in accordance with the invention has been found to introduce very little, if any, hydroxy compounds into the carvone, although the earlier stages of the usual synthesis from limonene do produce some hydroxy compounds.

In a preferred embodiment of the process defined herein, carvone, prepared according to the process of the present invention is purified according to the process described in U.S. Pat. No. 5,302,759, the teachings of which are hereby incorporated by reference, wherein the crude carvone is treated with an organometallic compound of formula $M(X)_n$, as hereinbefore defined. M is a polyvalent metal atom, preferably selected from titanium, aluminium or boron. n is the valence of the metal, i.e. l equals 4 for titanium and 3 for aluminium or boron. X is an alkoxy group, typically having 1 to 10 carbon atoms and preferably 1 to 4 carbon atoms. Particularly preferred alkoxy groups for use herein are methoxy, ethoxy, propoxy or butoxy.

Preferably, when the organometallic compound added is an alkoxide, there will be a by-product alcohol (e.g. isopropanol from tetraisopropoxytitanium) which is sufficiently volatile to be removed from the carvone before the carvone is distilled.

The amount of organometallic compound used will depend principally upon the amount of hydroxy compound present in the crude carvone product. Usually, the amount of $M(X)_n$ added to the crude carvone is sufficient to produce a molar ratio of $M(X)_n$ to hydroxy compound in the range 0.5:1 to 1.5:1 and preferably in the range 0.75:1 to 1:1.

The carvone produced according to the preferred process of the invention is particularly useful for dental flavourings and generally contains low levels of undesirable impurities.

The invention is illustrated by the following non-limiting examples.

EXAMPLE 1

To a mixture of pure L-carvoxime (10.07 g), 5% Pd on BaSC. catalyst (0.5672 g), and $Pb_3O_4$ (0.1325 g) in a Parr microautoclave were added acetic acid (15 ml) and water (10 ml). The mixture was flushed with nitrogen and then with hydrogen and heated to 100° C. under a hydrogen pressure of 4.5 MPa and maintained at that temperature and pressure for 23 hours. The progress of the reaction was followed by sampling the reaction mixture and analysing the samples taken by gas chromatography. The reaction mixture was found to have the following composition after 23 hours:

| Compound | Relative Peak Area % |
| --- | --- |
| Dihydrocarvones | 2.72 |
| L-Carvone | 95.37 |
| 5-Isopropenyl-2-methylphenol | 0.54 |
| Hydroxycarvone | 0.57 |

The chromatography conditions were as follows. System: Hewlett Packard HP 6890. Column: Model HP 19091J-412; HP-5 5% phenylmethylsiloxane capillary: 30 m×320 μm×0.25 μm nominal. Carrier gas: Nitrogen, pressure 0.11 MPa, flow 0.8 ml/min, average velocity 29 cm/sec. Program: 50° C., hold 5 minutes, ramp 10° C./min to 280° C., hold 15 minutes.

EXAMPLE 2

The outlet of an HPLC pump was connected to the Parr microreactor by stainless steel tubing (1.6 mm internal diameter).

A solution of 22.23% by weight pure L-carvoxime in acetic acid was prepared (by dissolving 35 g pure L-carvoxime in 122.4 g acetic acid). The bottle of the solution was placed on a balance and the inlet tube of the HPLC pump, equipped with a filter, held in position by a clamp, was dipped into the solution.

To a 100 ml Parr reactor, 20 ml acetic acid, 1 ml water, 0.0507 g catalyst (5% Pd on $BaSO_4$) and 0.0109 g red lead oxide were added. The reactor was then purged with hydrogen, pressurised (with hydrogen) to 4.59 MPa and heated at 127° C. The pump, set at a flow rate of 0.03 ml/min, was then turned on and the addition of the solution comprising L-carvoxime in acetic acid started. The temperature, pressure and weight of the L-carvoxime solution was monitored throughout the reaction. The addition was terminated after 5.5 hrs, during which time 16.70 g feed solution was added to the Parr reactor. The reaction was found to be incomplete. The reaction mixture was then stirred for an additional 8.5 hrs under the same conditions after which time the reaction was complete. The reaction mixture was cooled to room temperature (room temperature as used herein is 23° C.) and then filtered to obtain 35.754 g filtrate. This was then analysed by internal standard GC to determine the L-carvone content, which was found to be 7.1% by weight. The feed solution was found by internal standard GC to contain 19.1% by weight L-carvoxime. The yield of the reaction was 87.54%.

The chromatography conditions were as follows. System: Hewlett Packard HP 5890sII. Column: Model HP 19091Z102; capillary: 25 m×0.2 mm nominal. Carrier gas: Nitrogen, column flow 0.42 ml/min, average velocity 22.3 cm/sec, split flow 77.0 ml/min, split ratio 183:1. Program: 100° C. to 280° C. at 6° C. per min.

The Internal Standard GC procedure was as follows:

An internal standard solution was firstly prepared by weighing tridecane (1.00 g) in a 100 ml volumetric flask and making up to the mark with toluene (HPLC grade ex Fisher Scientific). The standard solution was mixed thoroughly before use.

Calibration Procedure

To calibrate the GC, nine standard solutions of each of carvone/carvoxime were prepared at varying concentrations by adding 0.0100, 0.0200, 0.0500, 0.1000, 0.1500, 0.2000, 0.2500, 0.30000, 0.5000 g of each to 10 ml volumetric flasks. To each volumetric flask, 1 ml of the internal standard (IS) solution was added via a syringe (part #:5182-9604 ex HP) and diluted to the 10 ml mark with toluene. The solutions were mixed thoroughly, and each solution prepared was run under the GC conditions described above. The peak area data obtained from each carvone/carvoxime and IS standard run was used to plot a graph of the peak area ratio (either carvone or carvoxime/IS) against the corresponding carvone/carvoxime concentration (g10 ml toluene). Using linear regression analysis, the gradient and y-intercept for a carvoxime/carvone plot was determined.

Analysis of Crude Product

To a volumetric flask (10 ml) was added a sample of dried crude reaction product (0.10–100 g) and internal standard solution (1 ml). The contents of the flask were then diluted to the 10 ml mark with toluene and mixed thoroughly, 1 ml of this solution was then injected into the GC.

The amount of carvone/carvoxime in the crude reaction product/feed solution was calculated as follows:

1. The peak area ratio was calculated for each plot wherein;

$$\text{peak area ratio} = \frac{\text{carvone/carvoxime peak area}}{\text{IS peak area}}$$

2. Using this ratio and the y-intercept and gradient from the calibration graph, the carvone/carvoxime content (%) in the product/solution was calculated as follows:

calculated mass of carvone/carvoxime (g)=[peak area ratio±y-intercept]/gradient then, % carvone/carvoxime =

$$\frac{[\text{calculated mass of carvone/carvoxime (g)}]}{[\text{weight of sample taken}]} \times 100$$

EXAMPLE 3

To a refluxing suspension of anhydrous sodium acetate (20 g) dissolved in water (40 ml), acetic acid (250 ml), 5% Pd on $BaSO_4$ catalyst (20 g), and red lead oxide (1.94 g), was added dropwise over 6 hours at 112–117° C., a solution of L-carvoxime in formic acid (534.27 g containing 36% carvoxime, prepared from d-limonene as hereinabove described). The reaction was further refluxed for another 8 hours. When, from GC analysis, the reaction was complete, it was cooled to room temperature. Deionised water (400 ml) was then added with stirring to the reaction mixture. The organic phase and aqueous phase were separated and the solvent of the organic layer was removed in vacuo to yield; 434.44 g of crude product. The crude product was found to contain 39.1% carvone by internal standard GC, (the method and chromatography conditions are as indicated above in Example 2), hence the yield of the reaction was 81.35%.

What is claimed is:

1. A process for the preparation of carvone comprising hydrogenating carvoxime in the presence of a selectively poisoned catalyst.

2. A process according to claim 1, wherein the product carvone, is L-carvone.

3. A process according to claim 1, wherein carvoxime is hydrogenated by heating the carvoxime in the presence of a hydrogen source and a selectively poisoned catalyst.

4. A process according to claim 3, wherein the hydrogen source is hydrogen gas.

5. A process according to claim 3, wherein the reaction is carried out at a pressure in the range 1.0 MPa to 10.0 MPa.

6. A process according to claim 3, wherein the hydrogen source is any compound which is a hydrogen donor.

7. A process according to claim 6, wherein the hydrogen donor is formic acid buffered by a salt.

8. A process according to claim 7, wherein the salt is sodium acetate.

9. A process according to claim 6, wherein the reaction is carried out at atmospheric pressure.

10. A process according to claim 1, wherein the carvoxime is hydrogenated at a temperature in the range 80° C. to 180° C.

11. A process according to claim 1, wherein the catalyst is a noble metal catalyst supported on a material, which is poisoned by mixing with a catalyst modifier.

12. A process according to claim 12, wherein the catalyst modifier is a lead compound.

13. A process according to claim 12, wherein the lead compound is red lead oxide.

14. A process according to claim 11, wherein the catalyst is palladium supported on barium sulphate poisoned by red lead oxide ($Pb_3O_4$).

15. A process according to claim 1, wherein the catalyst is present in an amount in the range 0.1% to 10.0% by weight of carvoxime.

16. A process according to claim 1, wherein the reaction mixture additionally comprises an acid which neutralises the ammonia by-product formed.

17. A process according to claim 16, wherein the acid is a carboxylic acid.

18. A process according to claim 16, wherein the carboxylic acid is acetic acid or formic acid.

19. A process according to claim 1, wherein additionally, the reaction product carvone is purified by treating the crude carvone product with an organometallic compound $M(X)_n$, wherein M is a polyvalent metal, n is a valence of M and X denotes an inorganic or organic atom or group.

20. A process according to claim 19, wherein M is selected from titanium, aluminium or boron.

21. A process according to claim 19, wherein X is an alkoxy group.

22. A process according to claim 19, wherein the amount of $M(X)_n$ added to the crude carvone is sufficient to produce a molar ratio of $M(X)_n$ to hydroxy compounds in the range 0.5:1 to 1.5:1.

* * * * *